United States Patent [19]

Creighton et al.

[11] Patent Number: 5,616,563
[45] Date of Patent: Apr. 1, 1997

[54] GLUTATHIONE N-HYDROXYCARBAMOYL THIOESTERS AND METHOD OF INHIBITING NEOPLASTIC GROWTH

[75] Inventors: Donald J. Creighton; Diana S. Hamilton, both of Baltimore, Md.

[73] Assignee: University of Maryland Baltimore Campus, Baltimore, Md.

[21] Appl. No.: 264,940

[22] Filed: Jun. 24, 1994

Related U.S. Application Data

[63] Continuation-in-part of Ser. No. 986,691, Dec. 7, 1992, abandoned.

[51] Int. Cl.$^6$ .................................................. A61K 38/06
[52] U.S. Cl. .......................... 514/18; 514/513; 558/240; 560/16; 560/153; 562/426; 562/556
[58] Field of Search ...................... 514/18, 513; 558/240; 560/16, 153; 562/426, 556

[56] References Cited

U.S. PATENT DOCUMENTS

| | | | |
|---|---|---|---|
| 4,108,854 | 8/1978 | Gleason et al. | 544/277 |
| 4,127,600 | 11/1978 | Fuchs | 260/455 A |
| 4,778,915 | 10/1988 | Lina et al. | 560/29 |
| 4,997,969 | 3/1991 | Luciani | 558/240 |
| 5,464,825 | 11/1995 | Anderson et al. | 514/18 |
| 5,466,673 | 11/1995 | Ohmori et al. | 514/18 |
| 5,541,162 | 6/1996 | Ohmori et al. | 514/18 |

OTHER PUBLICATIONS

Hamilton et al., "Inhibition of Glyoxylase I . . . S (N Hydroxy N methylcarbamoyl)glutathione", The J. of Biol. Chem., vol. 267, No. 35, Dec. 1992, pp. 24933 36.

Lo et al., "Inhibition of Proliferation of Human Leudaemia 60 cells by Diethyl Esters of Glyoxylase Inhibitors in vitro", Biol. Pharm., vol. 44, No. 12, 1992, pp. 2357 63.

T. W. Graham Solomons, "Organic Chemistry", 4th ed., 1988, p. 837.

"Feasibility of Drug Screening with Panels of Human Tumor Cell Lines Using a Microculture Tetrazolium Assay", Cancer Research 48, pp. 589–601, Feb. 1, 1988, Michael C. Alley, et al.

"Glutathione Monoesters", Analytical Biochemistry 183, pp. 16–20 (1989), Mary E. Anderson et al.

"Optimization of Efficiency in the Glyoxalase Pathway", reprinted from Biochemistry, 1988, vol. 27, pp. 7376–7384, Donald J. Creighton et al.

"Caution: The glycylmethyl and glycylethyl esters of glutathione are substrates for glyoxalase I", Biochimica et Biophysica Acta, 1159 (1992), pp. 203–208, by Diana S. Hamilton.

"Inhibition of Glyoxalase I by the Enediol Mimic S–(N–Hydroxy–N–methylcarbamoyl)glutathione", The Journal of Biological Chemistry, vol. 287, No. 35, Issue of Dec. 15, pp. 24933–24936, 1992, Donald J. Creighton et al.

"Feasibility of a High–Flux Anticancer Drug Screen Using a Diverse Panel of Cultured Human Tumor Cell Lines", Journal of the National Cancer Institute, vol. 83, No. 11, Jun. 5, 1991, pp. 757–766, Anne Monks et al.

"S–(N–Aryl–N–hydroxycarbamoyl)glutathione Derivatives Are Tight–binding Inhibitors of Glyoxalase I and Slow Substrates for Glyoxalase II", Journal of Medicinal Chemistry, vol. 37, No. 14, 1994, pp. 2161–2166, Murthy et al.

Primary Examiner—Gary Geist
Assistant Examiner—Rosalynd A. Williams
Attorney, Agent, or Firm—Burns, Doane, Swecker & Mathis, LLP

[57] ABSTRACT

A compound of the formula

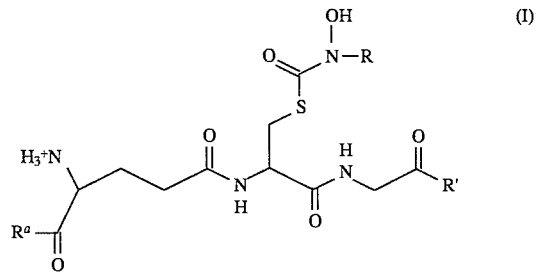

with R being hydrogen, alkyl, cycloalkyl or aryl, which may be substituted with halogen or alkyl, and R' and R$^a$ being hydroxyl, or —O-alkyl, pharmaceutically acceptable salts thereof; or mixtures thereof. An anti-neoplastic composition comprises the compound described above and a pharmaceutically acceptable carrier. In vitro and in vivo methods of preventing or inhibiting the growth and proliferation of neoplastic cells and/or tumors comprise contacting the cells with or administering to a subject an anti-growth and proliferation effective amount of the compound described above.

25 Claims, No Drawings

GLUTATHIONE N-HYDROXYCARBAMOYL THIOESTERS AND METHOD OF INHIBITING NEOPLASTIC GROWTH

CROSS-REFERENCE TO RELATED APPLICATION

This application is a continuation-in-part of U.S. Ser. No. 07/986,691, filed Dec. 7, 1992, now abandoned, which application is hereby incorporated by reference in its entirety.

BACKGROUND OF THE INVENTION

1. Field of the Invention

The present invention relates generally to the use of novel S(N-hydroxycarbamoyl) glutathione mono- and di-ester derivatives as potent cytotoxic and anti-tumorigenic agents, and to a method of treating tumorigenic diseases with these derivatives. More specifically, this invention relates to the use of S-(N-hydroxycarbamoyl) glutathione mono- and di-ester derivatives, and salts thereof, in suppressing and inhibiting tumorous and metasiatic growth in humans.

2. Description of the Background

Cancer can develop in the tissues of any organ at any age. The etiology of cancer is not clearly defined but mechanisms such as genetic susceptibility, chromosome breakage disorders, viruses, environmental factors and inmmunologic disorders have all been linked to malignant cell growth and transformation.

Tumorigenic growths are a most serious threat in modern times. Malignant or cancerous growths produce uncontrolled cell proliferation which results in unregulated growth of malignant tissue, lack of differentiation and an ability to invade local and even remote tissues. These growths have become, due to their unique characteristics, some of the most serious diseases encountered in modern medicine. Unfortunately, during the development of diseases associated with neoplastic growth there has been a lack of detectable symptoms and, for the most part, no completely effective therapy and/or prevention.

The seriousness of most cancer diseases and the lack of satisfactory treatment is accompanied by extreme secondary side effects found to accompany all current forms of cancer therapy. The success of surgery, the most radical treatment, depends on the stage when the cancer growth is discovered. If a whole tumor is discovered and removed before metastases develop, then surgery may be effective. In the majority of cases, however, the cancer is discovered too late for surgery to be effective as the sole treatment. Moreover, other available therapies, such as radiotherapy and chemotherapy, are accompanied by severe adverse reactions. In the case of radiotherapy, the sublethal doses of radiation used still adversely affect non-tumor tissues of the patient.

Anti-neoplastic chemotherapy currently encompasses various groups of drugs. Alkylating agents that alkylate cell protein and nucleic acids disrupt cell replication and metabolism and lead to cell death. Typical alkylating agents are nitrogen mustard, cyclophosphamide and chlorambucil. These agents are highly toxic and produce nausea, vomiting, alopecia, hemorrhagic cystitis, pulmonary fibrosis and an increased risk of development of acute leukemia. Purine, pyrimidine and folate antagonists are cell cycle and phase specific. In order to exert their anti-tumor effect, cells must be in the cell replication cycle and in the DNA synthesis phase of replication. Purine antagonists such as 6-mercaptopurine or 6-thioguanidine inhibit de novo purine synthesis and interconversion of purines. Pyrimidine antagonists, such as cytarabine, 5-fluorouracil or floxuridine inhibit DNA synthesis by inhibiting deoxycytidylate kinase and DNA polymerase. Folate antagonists such as methotrexate bind tightly to the intracellular enzyme dihydrofolate reductase, ultimately causing cell death from the inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. The toxicities of these drugs are similar to those described above and include myopathy, myelosuppression, peripheral neuropathy, vomiting, nausea and alopecia.

Anti-tumor antibiotics such as doxorubicin, daunorubicin and dactinomycin act as DNA intercalators, preventing cell replication, and inhibiting the synthesis of DNA-dependent RNA and DNA polymerase. Bleomycin causes the scission of DNA and mitomycin acts as an inhibitor of DNA synthesis by bifunctional alkylation. These antibiotics are extremely toxic and produce necrosis, myelosuppression, anaphylactic reactions, anorexia, dose-dependent cardiotoxicity and pulmonary fibrosis.

Other compounds used for the chemotherapy of cancer are inorganic ions such as cisplatin and biologic response modifiers such as interferon, and various hormones. These compounds, similar to those mentioned above, are accompanied by toxic adverse reactions, and their use is limited due to severe side effects.

Most of the chemotherapeutic cancer treatments described above specifically target rapidly dividing cells by inhibiting DNA/protein synthesis. Unfortunately, rapidly dividing normal cells, like those of the intestinal epithelium and bone marrow, are also adversely affected by these drugs. This accounts for the severe side effects associated with cancer chemotherapy. Recent studies by the inventors and others suggest that the glyoxalase pathway plays a critically important detoxification role in cells. The quantitative differences in the levels of the glyoxalase enzymes in normal tissues versus neoplastic tissues is the basis of the alternative chemotherapy of the invention.

The glyoxalase enzyme system is a simple metabolic pathway, composed of just two enzymes that function to chemically remove cytotoxic methylglyoxal from cells as D-lactate, as shown in Scheme 1:

SCHEME I

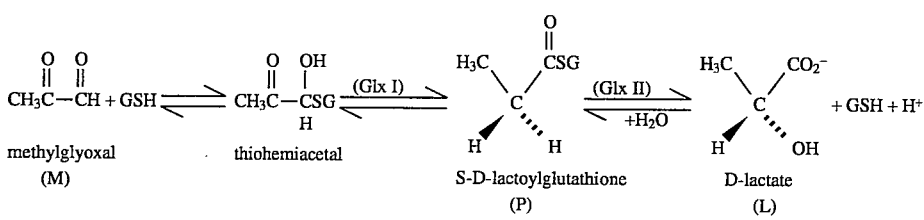

methylglyoxal (M) — thiohemiacetal — S-D-lactoylglutathione (P) — D-lactate (L)

Glyoxalase I (hereinafter referred to as "Glx I"), the first enzyme in the pathway, catalyzes the conversion of the thiohemiacetal formed by glutathione (GSH) and methylglyoxal (M) to S-D-lactylglutathione (P). Glyoxalase II (hereinafter referred to as "Glx II"), the second enzyme in the pathway, catalyzes the hydrolysis of S-D-lactoylglutathione (P) to D-lactate (L). Methylglyoxal has been shown to arise as an unavoidable by-product of the enzymatic and nonenzymatic isomerization of intracellular triosephosphates. Previous reports that formaldehyde dehydrogenase can efficiently use methylglyoxal as a substrate, thereby by-passing the glyoxalase pathway, appear to be erroneous. In support of a detoxification role for the glyoxalase pathway, a mutant strain of the yeast *Saccharomyces cerevisiae*, which is defective in Glx I, is eventually killed by exposure to glycerol due to the accumulation of intracellular methylglyoxal. Moreover, *E. coli* cells amplified with the gene for Glx I exhibit enhanced resistance to the growth-inhibitory effect of methylglyoxal. The substrate specificities and kinetic properties of the glyoxalase enzymes are consistent with a pathway whose purpose is to efficiently remove methylglyoxal from cells. A quantitative kinetic model for the conversion of methylglyoxal to D-lactate in erythrocytes has recently been formulated by the inventors that emphasizes the high level of kinetic efficiency of the pathway. The following two major conclusions emerge from this kinetic model.

a) The pathway overall is about 50% of maximal kinetic efficiency in the sense that the thiohemiacetal substrate partitions nearly equally between formation of D-lactate and specific-base catalyzed dissociation to form free methylglyoxal (M) and GSH. That is, the nonenzymatic rate of formation of the thiohemiacetal is significantly rate determining.

b) Both of the "diffusion-controlled" glyoxalase enzymes, i.e., enzymes whose efficiency is dependent upon the rate at which the substrate diffuses to the enzyme, are about 50% of maximal efficiency in the sense that bound substrates partition nearly equally between product formation and dissociation from the surface of the enzyme.

Thus, the pathway appears, at least in normal cells, to have achieved "optimal" kinetic efficiency in the sense that pathway velocity is now constrained by two fundamental physicochemical constants of water. These are the biomolecular rate of diffusion-controlled encounter between substrates and active sites, and the autoprotolysis constant of water that controls the specific-base catalyzed formation/decomposition of the thiohemiacetal at physiological pH 7. Presumably, this high level of kinetic efficiency arose during the course of biological evolution because of the selective advantage of minimizing the steady-state concentration of methylglyoxal in cells. This implies that the inhibition of the glyoxalase pathway should have severe deleterious effects on the cell.

From a historical perspective, early interest in the glyoxalase pathway as an anti-cancer target was based on reports that methylglyoxal has anti-neoplastic activity when tested against a range of different tumor types including Ehrlich ascites carcinoma, Yoshida ascites sarcoma, Kirkman-Robbins hamster hepatoma, adenocarcinoma, lymphosarcoma, and leukemia L4946. This effect might be due to inhibiting protein synthesis at the level of translation.

Indeed, certain S-aryl glutathione derivatives, known to be potent competitive inhibitors of Glx I, were found to inhibit the growth of L1210 leukemia and KB cells in culture (Vince et al., *J. Med. Chem.*, 14:35–37 (1971)). The particular derivatives and the results obtained therefrom are shown in Table 1.

TABLE 1

Inhibition of Glyoxalase I and L1210 and KB Cell Cultures by Glutathione Derivatives (GSR)

| No. | R | $I_{50a}$ (mM) | $LD_{50b}$ (L1210, mM) | $LD_{50b}$ (KB, mM) |
|---|---|---|---|---|
| 1 | $(CH_2)_2COC_6H_5$ | 0.077 | 0.08 | 0.07 |
| 2 | $CH_2C_6H_3Br$-P | 0.009 | >0.20 | 0.11 |
| 3 | $C_6H_2(NO)_3^{-2,4,6}$ | c | 0.12 | 0.05 |
| 4 | $C_6H_3(NO_3)_2^{-2,4}$ | 0.766 | >0.20 | 0.06 |

$_a I_{50}$ = concentration of 50% inhibition of glyoxalase I.
$_b$Concentration of compound for 50% kill of the cell culture.
$_c$No inhibitory activity was detected.

Vince et al., however, disclosed neither a clear correlation between the extent of cell growth inhibition and the $K_i$ values of the inhibitors, nor any reason to believe that highly charged GSH derivatives could diffuse across cell membranes. Thus, the observed cell growth inhibition could not be clearly ascribed to inhibition of intracellular Glx I. Nor did Vince et al. suggest how inhibition of Glx I could form the basis of a tumor-selective anticancer strategy.

The present inventors thus sought to overcome the problems of inhibitor transport and tumor-selectivity by using carefully designed inhibitors of Glx I. For example, based on the observation of Meister and coworkers that GSH[glycyl] ethyl ester is more rapidly transported than GSH into cells (Anderson et al., *Arch. Biochem. Biophys.*, 239:538–548 (1985)), the present inventors believed that derivatives of GSH might be delivered indirectly into cells as their ethyl esters. Once inside the cell, the ester will be catalytically hydrolyzed to give free GSH.

Regarding the Glx II enzyme of the glyoxalase pathway, it is known in the art that several different types of cancer cells contain reduced levels of glyoxalase II activity in comparison with normal cells (Jerzykowski et al., *Experientia* (Basel) 31:32–33 (1975); Jerzykowski et al., *Int. J. Biochem.* 9:853–860 (1978); and Thornalley, *Biochem. J.* 269:1–11 (1990). For example, a comparison of the activity of Glx I and Glx II in normal and cancer cells is set forth in Table 2, below.

TABLE 2

Some reported examples of glyoxalase activity in normal cells versus cancer cells

| | Glyoxalase (mU/mg protein) | | |
|---|---|---|---|
| Tissue | I | II | GlxI/GLxII |
| Normal Cells: | | | |
| Erythrocytes (human)[a] | 129 ± 32 | 50 ± 13 | 2.6 |
| Brain (human)[a] | 1113 ± 19 | 817 ± 156 | 1.4 |
| Liver (human)[a] | 209 ± 56 | 360 ± 13 | 0.6 |
| Heart (hamster)[a] | 339 ± 24 | 280 ± 47 | 1.2 |
| Kidney (human)[a] | 323 ± 48 | 330 ± 86 | 1.0 |
| Tumor cells: | | | |
| Leukemia 1210 (mouse)[a] | 113 ± 56 | ~0 | large |
| Glioblastoma (human)[a] | 290 ± 56 | 53 ± 10 | 5.5 |
| Kirkman-Robbins hepatoma (hamster)[a] | 540 ± 48 | 40 ± 10 | 13.5 |
| Fibroadenoma mammae (human)[a] | 419 ± 73 | 27 ± 7 | 15.5 |
| Bladder HT1197 (human)[b] | 542 ± 38 | 8 ± 1 | 67.8 |
| Kidney OUR10 (human)[b] | 321 ± 86 | 44 ± 16 | 7.3 |
| Prostate PC3 (human)[b] | 4206 ± 294 | 45 ± 3 | 93.4 |
| Testis T1 (human)[b] | 4767 ± 275 | 94 ± 12 | 51.0 |
| Colon HT29 (human)[b] | 542 ± 59 | 11 ± 1 | 49.3 |

[a] Jerzylowski, et al., Int. J. Biochem. 9:853 (1978).
[b] Ayoub, et al., Anticancer Res. 13:151 (1993).

In view of the above, there thus exists a need in the art for GSH derivatives which are sufficiently hydrophobic to transport across the cell membrane into cells, for example, as their alkyl esters, and which will be subject to intracellular hydrolysis to produce free GSH.

In addition, there is a need in the art for compounds which will selectively inhibit or retard the growth and proliferation of neoplastic cells without affecting normal cells in vivo. In this regard, there is a need in the art for competitive inhibitors of Glx I that also serve as substrates for Glx II. It is believed that such compounds would function as tumor-selective anti-cancer agents, based on the observation that Glx II activity is abnormally low in some types of tumor cells. These inhibitors could, therefore, induce higher steady state concentrations of cytotoxic methylglyoxal in tumor cells than in normal cells because of the reduced ability of tumor cells to hydrolyze the inhibitor.

There is also a need in the art for pharmaceutical compositions useful for inhibiting or retarding the growth and proliferation of neoplastic cells and/or a tumor in a mammal which is not susceptible to multi-drug resistance. Multi-drug resistance is due to decreased accumulation of drugs in cells caused by increased drug efflux and/or decreased cell permeability mediated by the multi-drug transporter protein. This will occur for hydrophobic natural products, semi-synthetic analogs of such products, and synthetic organic compounds which are amphipathic and preferentially soluble in lipid. There thus exists a need in the art for pharmaceutical compositions comprising compounds to which multi-drug resistant cells are not resistant.

Finally, there is a need in the art for a novel method of inhibiting or preventing the growth of neoplastic cells and/or a tumor in a mammal. A method which selectively inhibits or prevents the growth of neoplastic cells and/or a tumor without inhibiting or preventing the growth of normal cells would be desirable in the art.

OBJECTS AND SUMMARY OF THE INVENTION

It is an object of the present invention to provide GSH derivatives which are sufficiently lipophilic to transport across the cell membrane into cells and which are subject to intracellular modification to prevent their efflux from the cell. For example, it is an object of the present invention to provide alkyl ester derivatives of GSH, which derivatives are subject to intracellular hydrolysis.

In addition, there is a need in the art for competitive inhibitors of Glx I that also serve as substrates for Glx II. It is believed that such compounds would function as tumor-selective anticancer agents, based on the observation that Glx II activity is abnormally low in some types of tumor cells. These inhibitors could, therefore, induce higher steady state concentrations of cytotoxic methylglyoxal in tumor cells than in normal cells because of the reduced ability of tumor cells to hydrolyze the inhibitor.

It is a further object of the present invention to provide a method of inhibiting or preventing the growth of neoplastic cells and/or a tumor in a mammal, which method does not inhibit or prevent the growth of normal cells.

It is thus a general object of the present invention to provide a class of inhibitors of this type that have tumor-selective anticancer activity.

In general, this invention relates to GSH derivatives which are lipophilic, allowing their transport across cell membranes. Such GSH derivatives comprise alkyl ester substituents, which alkyl groups render the GSH derivatives hydrophobic and allow their transport across cell membranes. More specifically, this invention thus relates to compounds of the chemical formula

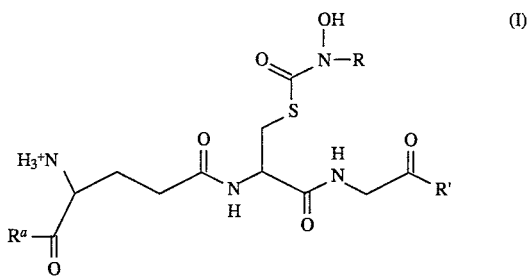

wherein

R is hydrogen, $(C_1-C_{18})$alkyl, $(C_6-C_{20})$cycloalkyl, or $(C_6-C_{20})$aryl which may be substituted with halogen or $(C_1-C_{18})$alkyl, and R' and $R^a$, which may be the same or different, are hydroxyl, $-O-(C_1-C_{18})$alkyl, pharmaceutically-acceptable salts thereof, or mixtures thereof.

A further aspect of this invention is an anti-neoplastic composition comprising at least one compound of the invention; and a pharmaceutically-acceptable carrier therefor.

This invention also relates to a method of inhibiting or retarding the growth and proliferation of neoplastic cells comprising treating the cells with an anti-growth and anti-proliferation effective amount of a compound of the invention or a composition thereof.

Also part of this invention is a method of inhibiting or preventing the growth of neoplastic cells and/or a tumor in a mammal comprising administering to a subject in need of such treatment an effective amount of a compound of the invention or a composition thereof.

A further aspect of the present invention is an in vitro method of preventing or inhibiting the growth and proliferation of, or eliminating neoplastic cells and/or a tumor in mammalian tissue comprising neoplastic cells or a tumor, wherein the method comprises treating the tissue comprising neoplastic cells or tumor with a compound of the invention or a composition thereof in an amount effective to inhibit or retard the growth and proliferation of, or eliminate said neoplastic cells or tumor from mammalian tissue. Such a method would be useful, for example, for tissue transplants such as bone marrow transplants. In such methods, the tissue may be removed from a mammal, treated according to the above described method, and reintroduced into said mammal or transplanted to a different mammal.

Other objects, advantages and features of the present invention will become apparent to those skilled in the art from the following discussion.

DESCRIPTION OF THE PREFERRED EMBODIMENTS

This invention arose from a desire of the inventors to improve on their previous work aimed at treating neoplasias with S-(N-hydroxycarbamoyl) glutathione derivatives capable of inhibiting the glyoxalase pathway.

The inventors have found that the present S-(N-aryl-N-hydroxycarbamoyl) glutathione derivatives are substrates for the Glx II enzyme, as well as excellent inhibitors of the Glx I enzyme. These compounds have been shown to retard or inhibit the growth of human renal cancer cells, ovarian cancer cells, colon cancer cells, melanoma cells, non-small cell lung cancer cells, central nervous system (CNS) cancer cells and leukemia cells, among others. Moreover, the dialkyl ester derivatives, in particular the diethyl ester derivatives, were found to be even more potent inhibitors of human leukemia 60 cells than the unesterified derivatives, apparently because of the more rapid rate of transport of the diethyl ester into cancer cells. In addition, these compounds selectively inhibit the growth of human leukemia 60 cells versus normal human fibroblasts.

As shown above in Table 2, abnormally low levels of Glx II activity have been found in many types of cancer cells. On this basis, the inventors conceived that competitive inhibitors of Glx I, which also serve as substrates for Glx II, might function as potent tumor-selective anti-cancer agents, given the reduced ability of cancer cells to hydrolyze such inhibitors. This, in turn, would result in higher steady-state concentrations of cytotoxic methylglyoxal in cancer cells than in normal cells.

The compounds of the invention were designed to mimic the stereo-electronic features of the enediol(ate) intermediate that has been well established to form along the reaction pathway of Glx I, as shown below: Thus, they are predicted to bind tightly to the enzyme, on the basis of the theory that enzymes catalyze reactions by preferentially binding intermediates/transition states versus substrates and products. Indeed, the inventors have found that one of the compounds of this invention, S-(N-hydroxy N-methylcarbamoyl) glutathione, binds over 30-fold more tightly to yeast Glx I (Ki=0.068 mM)

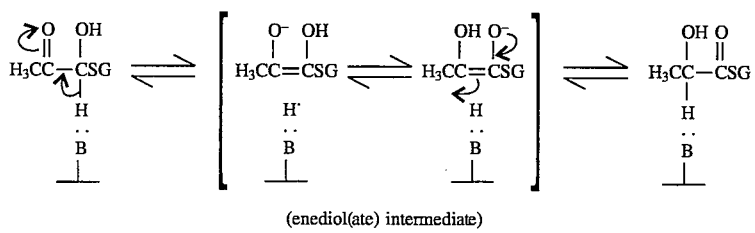

(enediol(ate) intermediate)

than the product of the Glx I reaction, S-D-lactoylglutathione (Ki=2.23 mM). Other compounds provided herein, such as S-(N-hydroxy N-4-bromophenylcarbamoyl) glutathione, were shown to be the strongest inhibitors of yeast Glx I (Ki=0.00 mM) and human erythrocyte Glx I (Ki=0.000016 mM) ever discovered when compared with other compounds such as those shown in Table 1, above. Clearly, the compounds of the invention are able to powerfully inhibit Glx I and reduce the rate of removal of the intracellular thio-hemiacetal formed by GSH and methylglyoxal. The intracellular build-up of thio-hemiacetal will, in turn, increase the concentration of intracellular methylglyoxal by a mass-action effect.

The compounds of the invention also function as substrates for the hydrolase Glx II, of which cancer cells have lower levels than do normal cells. This property most likely enables the compounds to cause a disproportionately larger increase in the intracellular levels of methylglyoxal in cancer cells over normal cells. In norman cells the compounds of the invention will be hydrolyzed and the inhibitor compound thus removed from the Glx I enzyme. Due to the higher level of Glx II in normal cells than in cancer cells, the inhibitor compound will be removed from the Glx I enzyme at a higher rate in normal cells and, thus, increase the amount of Glx I enzyme available to normal cells for the metabolism of methylglyoxal. The slower rate of hydrolysis of the compounds by cancer cells will, in turn, maintain the inhibition of Glx I and disrupt the metabolism of methylglyoxal. Methylglyoxal will thus accumulate in cancer cells.

The compounds of the invention are designed to be rapidly taken up by the cells, i.e., transported across cell membranes. The inventors have found that the glycyl-O-alkyl esters of the compounds of the invention are more rapidly taken up by human red blood cells (a model cell system) than the corresponding non-esterified compounds. The facile transport of the glycyl-O-ethyl esters is possibly due to the absence of a negative charge on the glycyl moiety of the compounds and/or to the greater lipophilicity and hydrophobicity of the esters in comparison to the non-esterified compounds. The inventors have also found that the glycyl-O-ethyl ester compounds are converted intracellularly to their non-esterified compounds.

This invention thus provides a class of compounds of the chemical formula

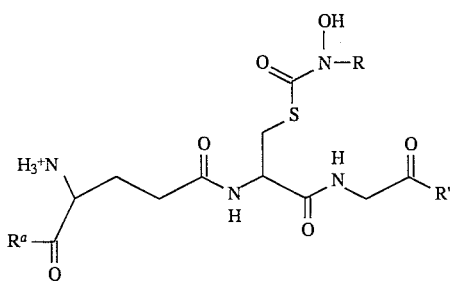

wherein

R is selected from the group consisting of hydrogen, (C1–C18)alkyl, (C6–C20)cycloalkyl, and (C6–C20)aryl which may be substituted with halogen or (C1–C18)alkyl, R' and $R^a$, which may be the same or different, are selected from the group consisting of hydroxyl and —O($C_1$–$C_{18}$)alkyl; pharmaceutically-acceptable salts thereof; and mixtures thereof.

Also part of this invention is an anti-neoplastic composition comprising at least one compound of the invention; and a pharmaceutically-acceptable carrier therefor.

As used herein, (C1–C18)alkyl refers to saturated and unsaturated, branched and straight chain hydrocarbon chains having 1 to 18 carbon atoms, which may be substituted with halogen, O, N or S. As used herein, (C6–C20)cycloalkyl and aryl, and (C6–C20)cycloalkyl and aryl substituted with halogen or (C1–C18)alkyl, refer to all cyclic and aromatic compounds having one or more rings and all structural isomers thereof.

One group of compounds in accordance with the invention is that of chemical formula I, wherein R is (C1–C18)alkyl or substituted alkyl, and pharmaceutically acceptable salts thereof. The S-(N-hydroxy N-(C1–C18)alkyl carbamoyl) glutathione esters may be synthesized by N-acylation of the corresponding N-(C1–C18)alkyl hydroxylamine with 4-chlorophenyl chloroformate according to the procedure of Gröbner et al. to form the 4-chlorophenyl ester of the desired N-hydroxycarbamate, followed by an acyl-interchange (thioesterification) reaction between the 4-chlorphenyl ester and glutathione (Gröbner et al., *Eur. J. Med. Chem. Cim. Ther.* 9:341–343 (1974)).

Preferred amongst these compounds, are compounds of formula I, wherein R is a lower alkyl, e.g., methyl or ethyl, and pharmaceutically acceptable salts thereof. The S-(N-hydroxy N-methylcarbamoyl) and S-(N-hydroxy N-ethylcarbamoyl) esters of glutathione may be synthesized by N-acylation of N-methylhydroxylamine or N-ethylhydroxylamine, respectively, with 4-chlorophenylchloroformate to form the 4-chlorophenyl esters of N-hydroxy N-methylcarbamate and N-hydroxy N-ethylcarbamate, followed by an acyl-interchange reaction between the corresponding 4-chlorophenyl ester and glutathione.

Another preferred group of compounds of chemical formula I is that where R' and $R^a$ are an O—(C1–C18)alkyl, preferably an O—(C1–C10)alkyl, more preferably an O—(C1–C6)alkyl, and most preferably an O—ethyl; and pharmaceutically acceptable salts thereof. These S-(N-hydroxycarbamoyl) glutathione-O—(C1–C18)alkyl esters may be synthesized by O—(C1–C18)alkyl esterification of glutathione according to the general method of Anderson et al., followed by thioesterification of the desired glutathione-O—(C1–C18)alkyl ester with a 4-chlorophenyl ester of the desired N-hydroxy-carbamate (Anderson, et al., *Anal. Biochem.* 183:16–20 (1989)).

Also preferred is a group of compounds of chemical formula I, where R is a (C6–C20) cycloalkyl or aryl, and pharmaceutical salts thereof. These S-(N-hydroxy N—(C6–C20) cycloalkyl carbamoyl) and S-(N-hydroxy N—(C6–C20) arylcarbamoyl) esters of glutathione may be synthesized by N-acylation of the desired N—(C6–C20) cycloalkyl N—(C6–C20) aryl-hydroxylamine with 4-chlorophenylchloroformate to form a 4-chlorophenyl ester of the desired N-hydroxy N—(C6-C20) cycloalkyl carbonate or N-hydroxy N-(C6–C20) arylcarbamate, followed by thioesterification of glutathione with the 4-chlorophenyl ester.

Particularly preferred is a group of compounds of chemical formula I, wherein R is phenyl or 4-halophenyl, particularly 4-bromophenyl, and pharmaceutical salts thereof. These S-(N-hydroxy N-phenylcarbamoyl) and S-(N-hydroxy N-4-halophenylcarbamoyl) esters of glutathione may be synthesized by N-acylation of N-phenylhydroxylamine and N-4-halophenyl-hydroxylamine, respectively, with 4-chlorophenyl chloroformate to form 4-chlorophenyl esters of N-hydroxy N-phenylcarbamate and N-hydroxy N-4-halophenylcarbamate, followed by thioesterification of glutathione with the 4-chlorophenyl esters.

Another group of preferred compounds has the chemical formula I, wherein R and $R^a$ are (C1–C18)alkyl or (C6–C20)aryl and R' is O—(C1–C18)alkyl, preferably an O—(C1–C10)alkyl, more preferably an O—(C1–C6)alkyl, and pharmaceutical salts thereof. Particularly preferred are the S-(N-hydroxy N-methylcarbamoyl) glutathione O-ethyl ester, and the S-(N-hydroxy N-4-halophenylcarbamoyl) glutathione O-ethyl esters, and pharmaceutical salts thereof.

Examples of some of the most preferred compounds of chemical formula I are given below.

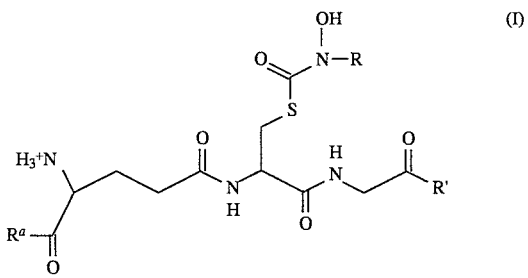

wherein

| Compound | R | R' and $R^a$ |
|---|---|---|
| 2 | —CH3 | —OC2H5 |
| 6a | —C6H5 | —OH |
| 6a(Et)2 | —C6H5 | —OC2H5 |
| 6b | —C6H4Cl | —OH |
| 6b(Et)2 | —C6H4Cl | —OC2H5 |
| 6c | —C6H4Br | —OH |
| 6c(Et)2 | —C6H4Br | —OC2H5 |

These S-(N-aryl N-hydroxycarbamoyl) glutathione derivatives have been found by the present inventors to transport across the cell membrane, be extremely strong inhibitors of the Glx I enzyme and serve as substrates for the Glx II enzyme, as shown in the examples of this application. Moreover, some of these compounds were found to serve as powerful tumor selective anti-cancer agents in tissue culture.

Pharmaceutical salts thereof suitable for administration by a variety of routes are known in the art and need not be described herein in detail. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium), ammonium, and NWnHm bases and salts wherein each of n and m are 0 to 4 and n+m is 4, and wherein W is a (C1–C18)alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-toluylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as Na+, and $NW_nH_m$, wherein W is a $(C_1–C_{18})$alkyl group, and n and m are 0 to 4, and n+m is 4.

Still part of this invention is a composition of matter that comprises the compound described above, mixtures thereof, and/or pharmaceutical salts thereof, and a pharmaceutical carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of inhibiting or retarding the growth and proliferation of neoplastic cells or tumors, a compound of formula I or its salt can be conveniently administered in the form of a pharmaceutical composition containing the formula I compound or its salt and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants and the like. Typically, the carrier may be a solid, liquid or vaporizable carrier, or combinations thereof. In one preferred embodiment, the composition is a therapeutic composition and the carrier is a pharmaceutically-acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous and intradermal) administration, with parenteral formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The compound of the invention may be present in the composition in a broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

Also part of this invention is a method of inhibiting or retarding the growth and proliferation of neoplastic cells comprising treating the cells with an anti-growth and proliferation effective amount of the compound of this invention. In this application, "treating" will encompass any means by which the compound of this invention contacts the neoplastic or tumor cells such that the compound is transported across the cell membrane into the cell.

A neoplastic cell or tumor is preferably treated with the compound of the present invention, pharmaceutically acceptable salts or mixtures thereof, at a preferred concentration of about 0.1 µM to 10 mM, more preferably about 0.1 to 1 mM, and still more preferably about 10 to 500 µM.

The invention also provides a method of inhibiting or preventing the growth of neoplastic cells in a subject comprising administering to a patient an effective amount of the composition of this invention comprising any of the compounds of chemical formula I, pharmaceutically-acceptable salts thereof, or mixtures thereof.

Also provided herein is a method of preventing or retarding the growth of a malignant tumor comprising administering to a subject in need of such treatment an effective amount of any of the compounds or the composition of the invention.

The present compounds are designed to be effective for the treatment of neoplasias and tumors in patients including humans and other mammals, such as renal cancers, breast cancers, bladder cancers, ovarian cancers, colon cancers, prostate cancers, testes cancers, melanomas, non-small cell lung cancers, CNS cancers, and leukemias, among others.

The dosage of the compound of formula I, pharmaceutically-acceptable salts or mixtures thereof, in the compositions of the invention administered to a patient will vary depending upon several factors, including, but not limited to, the age and weight of the patient, the type of cancer cells or tumors treated, how advanced and invasive the cancer is, the general health of the patient, the location of the tumor, the severity of the symptoms, whether the compound of formula I is being administered alone or in combination with other cancer therapies or other active ingredients, the incidence of side defects and the like.

In general, a dose suitable for application in the treatment of the abovementioned conditions is about 0.001 to 100 mg/kg body weight/dose, preferably about 0.01 to 60 mg/kg body weight/dose, and still more preferably of about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above identified variety of parameters. Typically, the present compound may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline, or orally administered as a bolus.

The compound according to the invention, also referred to herein as the active ingredient, may be administered for therapy by any suitable routes, including oral, rectal, nasal, vaginal and parenteral (including intraperitoneal, subcutaneous, intramuscular, intravenous and intradermal) routes. It will be appreciated that the preferred route will vary with the condition and age of the patient, the nature of the disorder and the chosen active ingredient including other therapeutic agents. Preferred is the intravenous route. However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including anti-neoplastic compounds, and/or therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective for the treatment of malignant cell growth, metastasis, and/or associated conditions in humans. Examples are alkylating agents such as nitrogen mustard, cyclophosphamide and chlorambucil, purine antagonists such as 6-mercaptopurine and 6-thioguanidine, pyrimidine antagonists such as cytarabine, 5-fluorouracil and floxuridine, folate antagonists such as methotrexates, plant alkaloids such as vincristine, vinblastine and podophyllotoxins such as doxorubicin, daunorubicin, dactinomycin, bleomycin and mitomycin, inorganic ions such as cisplatin, biological response modifiers such as interferon, enzymes, and hormones, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The chemotherapeutic method of the invention may be used in conjunction with other chemotherapies, radiotherapy and/ or surgery, as determined by the practitioner. Following surgery, the method of the invention may be used to prevent or inhibit the recurrence of malignant cell growth.

Further provided herein is an in vitro method of inhibiting or retarding the growth and proliferation of, or eliminating neoplastic cells and/or a tumor in mammalian tissue samples which comprises neoplastic cells or a tumor, wherein the method comprises treating neoplastic cells or tumor with an effective amount of any of the compounds or compositions of the invention. For such a method, the tissue sample may be treated with the compounds of the invention alone, or in combination with other chemotherapies and/or radiation therapy, as determined by the practitioner. The dialkyl ester derivatives of the compound of formula I are particularly preferred in this method; with the diethyl ester derivatives being the most preferred.

Such chemotherapeutic methods are generally known in the art. For example, the cancerous tissue will be removed from the patient for treatment, the tissue will be treated in accordance with this method of the present invention. Once the cancerous cells have been eliminated and/or their growth inhibited or retarded, the tissue may be reintroduced into the patient or transplanted to a different mammal. While this method has been generally described, the specifics of performing such a method would be readily apparent to one skilled in the art, for example, to an oncologist and/or surgeon, who has performed similar procedures with prior art chemotherapeutic compounds. Such methods are commonly used, for example, for treating bone marrow cancer.

The dosage of the compound of formula I administered in vitro to the tissue will vary depending upon several factors, for example, the type of cancer cells or tumors treated, the type of tissue treated, how advanced and invasive the cancer is, the particular compound of formula I employed, and whether the compound is being administered alone or in combination with other chemotherapeutic compounds and/ or radiation therapy.

In general, a concentration of the compound of formula I of about $10^{-2}$M to $10^{-6}$M is employed. Preferably, a concentration of about $10^{-3}$M to $10^{-5}$M is employed. The compounds may be administered to the tissue and then cell growth inhibiting/retardation and/or cell killing measured. If necessary, additional amounts of the compound of formula I may then be administered until the desired levels of cell growth inhibition/retardation and/or cell killing are obtained.

Having now generally described this invention, the same will be better understood by reference to certain specific examples, which are included herein for purposes of illustration only and are not intended to be limiting of the invention or any embodiment thereof, unless so specified.

EXAMPLES

Materials, Synthetic Methods and Analytical Procedures

S-(N-methyl N-hydroxycarbamoyl) glutathione (2) was prepared by reacting glutathione with N-methyl N-hydroxycarbamate 4-chlorophenyl ester. The S-(N-aryl N-hydroxycarbamoyl) glutathione derivatives 6(a), 6(b), and 6(c) were prepared by the reaction of glutathione (GSH) and the 4-chlorophenyl esters of the corresponding N-aryl N-hydroxycarbamates 5(a), 5(b), and 5(c) as outlined in Scheme II below. The crude products were purified to apparent homogeneity by reverse-phase high pressure liquid chromatography (HPLC).

SCHEME II

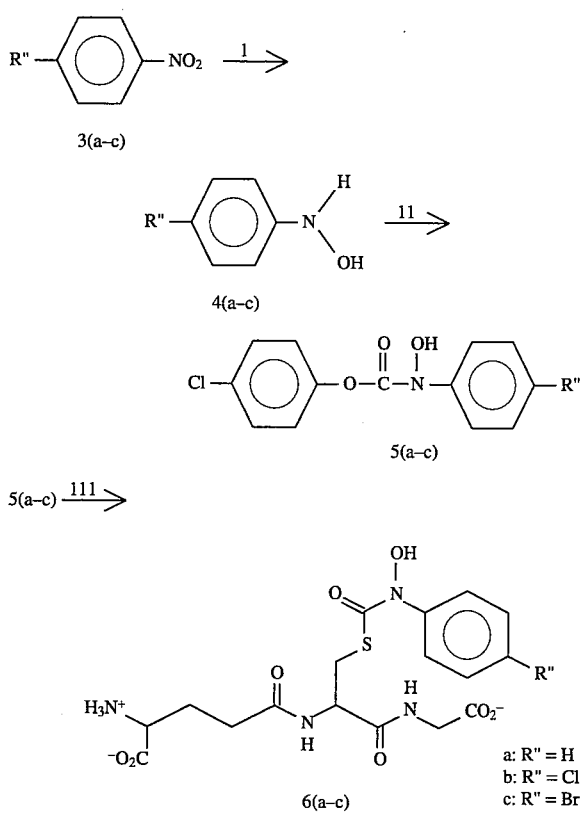

Reagents and conditions:
(i) e.g., N₂H₄/5% Rh on carbon/THF
(ii) 4-chlorophenyl chloroformate/K₂CO₃/EtOH
(iii) GSH/EtOH—H₂O The acylating reagents 5(a), 5(b), and 5(c) were prepared by a modification of a known procedure. (Gröbner et al, *Eur. J. Med. Chem. Chem. Ther.* 9:341 (1974)).

The hydroxylamines were prepared by reduction of the corresponding p-substituted nitrobenzenes 3(a), 3(b), and 3(c) using the known methods of Kamm for N-phenylhydroxylamine 4(a), of Entwistle et al. for N-p-chlorophenyl hydroxyl-amine 4(b), and Cummings et al. for N-p-bromophenylhydroxylamine 4(c). (Kamm, O., Organic Syntheses 1:445 (1941); Entwistle et al., *Tetrahedron* 34:213 (1978); Cummings et al., *J. Chem. Soc. Perin Trans. II*, pp.105–108 (1983)).

S-(N-methylcarbamoyl)glutathione was synthesized by reacting GSH with methyl isocyanate as described by Han et al. (Han et al., *J. Labelled Compd. Radiopharm.* 27:1371 (1989)).

S-propionyl glutathione was prepared by the acyl-interchange reaction between glutathione and S-propionyl thiophenol as described by Wieland and Koppe. (Wieland et al., *Justis Liebig Ann. Chem.* 588:15 (1954)).

The nuclear magnetic resonance (NMR) spectral assignments were done based on comparisons with previously published NMR studies of glutathione and its derivatives. (Rabenstein et al., "Nuclear Magnetic Resonance Spectroscopy of Glutathione," in *Coenzymes and Cofactors: Glutathione*, Dolphin et al., Eds., John Wiley, New York, Vol. 3 (A), pp. 67–101 (1989)).

The melting points were determined on a Mel-Temp apparatus and are uncorrected. All analytical samples were homogeneous as determined by TLC. NMR spectra were taken on a GE QE-300 NMR spectrometer (Midwest Center for Mass Spectrometry, University of Nebraska-Lincoln).

The preparations of yeast Glx I and bovine liver glyoxalase II were purchased from Sigma Chem. Co.

Human erythrocyte Glx I was purified to homogeneity from out-dated human blood by the procedure of Aronson et al. (Aronson et al., *Anal. Biochem.* 92:390 (1979)).

The magnitudes of the kinetic constants of compounds 6(a), 6(b), and 6(c) for Glx I and Glx II were determined as previously described by Hamilton et al. (Hamilton et al., *J. Biol. Chem.* 267:24933 (1992)).

The standard errors for $V_m$ and $K_m$ were obtained by analysis of the initial rate data using the HYPER program of Cleland. (Cleland, "The Statistical Analysis of Enzyme Kinetic Data", in *Adv. Enzymol.*, Nord, Ed., John Wiley, New York, Vol. 29, 1–32 (1967)).

EXAMPLE 1

Synthesis of (N-Hydroxy N-Methyl Carbamate)

4-Chlorophenyl Ester (N-Hydroxy N-methylcarbamate) 4-chlorophenyl ester was prepared by N-acylation of N-methylhydroxylamine with 4-chlorophenylchloroformate using a modification of the procedure described by Gröbner, P. et al. (Gröbner, P. et al., *Eur. J. Med. Chem. Chem. Ther.* 9:341–343 (1974)).

A solution of 4-chlorophenylchloroformate (4.8 g, 25 mmol) in dimethyl ether (20 ml) was added dropwise to an ice-cold stirring mixture of finely powdered N-methylhydroxylamine hydrochloride (2.4 g, 29 mmol), finely powdered K₂CO₃ (4.0 g, 29 mmol), dimethyl ether (80 mL) and water (1 mL) over a period of 30 min. The reaction mixture was allowed to come to room temperature and followed to completion (~1 h) by silica gel thin layer chromatography (TLC), using dimethyl ether:hexane (1:1) as a running solvent to produce (N-hydroxy N-methylcarbamate) 4-chlorophenyl ester, $R_f$=0.19; 4-chlorophenylchloroformate, $R_f$=0.60. The ether layer was removed, washed with water (2×20 ml), and the solvent removed in vacuo. The residue was recrystallized from methanol/water to give the final product as white needle-like crystals.

Yield: 96% m.p: 120°–121° C.

IR (KBr, 1%): –3200, 1720, 1685, 1490, 1220, 1150, 805 cm⁻¹.

H-1 300 MHz NMR (CDCl₃, TMS) –δ3.36 (s, CH₃), δ6.98 (s, OH), δ7.04–7.38 (aromatic ring H, m)

Electron-impact mass spectrum: m/z 201 (4%) [M]⁺•; 128 (100%) [ClC₆H₄OH]⁺•; 111 (6%) [ClC₆H₄]⁺•; 74 (10%) [C(O)N(OH)CH₃]⁺•.

EXAMPLE 2

Synthesis of S-(N-Hydroxy N-Methyl Carbamoyl) Glutathione (2) and [³⁵S] S-(N-Hydroxy N-Methylcarbamoyl) Glutathione ([³⁵S] 2)

S-(N-Hydroxy N-methylcarbamoyl) glutathione and [³⁵S] S-(N-hydroxy N-methylcarbamoyl) glutathione was synthesized by acyl-interchange reactions between (N-hydroxy N-methylcarbamate)4-chlorophenyl ester and glutathione (GSH) or [³⁵S]GSH, respectively.

S-(N-hydroxy N-methylcarbamoyl) glutathione, for example, was prepared by incubating GSH (0.31 g, 1 mmol) and (N-hydroxy N-methylcarbamate) 4-chlorophenyl ester (0.20 g, 1 mmol) in 6 mL methanol: 1N NaOH (2:1) at room temperature under argon until little GSH remained (90 h), as monitored by silica gel TLC (n-propanol:acetic acid:water (10:1:5) S-(N-hydroxy N-methyl-carbamoyl) glutathione, $R_f$=0.37; GSH, $R_f$=0.33; GSSG, $R_f$=0.09). The reaction mixture was acidified to pH 3.5 with HCl and extracted with dimethyl ether (3×10 mL). The aqueous phase was fractionated by reverse-phase HPLC (Whatman Partisil $C_{18}$, 2.2×50 cm) using 0.25% acetic acid in water as an eluting solvent, and the peak fractions lyophilized to give the final product as a white powder (retention volume: ~500 mL).

Yield: 50%

H-1 300 MHz NMR ($D_2O$, pD 3.5, DSS): $-\delta 2.15$ (Glu-C$\beta H_2$, m), $\delta 2.51$ (Glu-C$_\gamma H_2$, m), $\delta 3.13$ (Cys-C$\beta H_a$, q, J=8.2, 14.6 Hz), $\delta 3.26$ (N—CH$_3$, s), $\delta 3.38$ (Cys-C$\beta H_b$, q, J=5.0, 14.6 Hz), $\delta 3.81$ (Glu-C$\alpha$H, t, J=6.3 Hz), $\delta 3.96$ (Gly-CH$_2$, s), $\delta 4.63$ (Cys-C$\alpha$H, q, J 5.0, 8.2 Hz)

Tandem FAB mass spectrum: m/z (rel. intensity) −381 [M+H]$^+$; 307 (100%) [M-C(O)N(OH)CH$_3$+H]$^+$; 252 (29%) [M-C(O)CH$_2$CH$_2$CH(CO$_2$H)NH$_2$+2H]$_+$; 130 (79%) [H$_2$NCH(CO$_2$H) CH$_2$CH$_2$CO]$^+$; 76 (53%) [H$_3$NCH$_2$CO$_2$H)]$^+$.

EXAMPLE 3

Preparation of Glutathione[Glycyl]-O-Ethyl Ester

The glutathione[glycyl]-O-ethyl ester (HCl salt) was synthesized by the procedure described by Anderson et al. (Anderson et al. (1989), supra). The crude product was then purified by reverse phase HPLC (Waters μBondapak C-18, 0.78×30 cm) using 0.25% acetic acid in water as an eluting solvent (Elution volume of glutathione[glycyl]-O-ethyl ester 1:40–40 mL).

EXAMPLE 4

Synthesis of S-(N-Hydroxy N-Methyl-Carbamoyl) Glutathione [Giycyl]-O-Ethyl Ester and [$^{35}$S] S-(N-Hydroxy N-Methyl Carbamoyl) Glutathione [Glycyl]-O-Ethyl Ester The S-(N-Hydroxy N-methylcarbamoyl) glutathione[glycyl]-O-ethyl ester and [$^{35}$S]S-(N-hydroxy N-methylcarbamoyl)glutathione[glycyl]-O-ethyl ester were synthesized by the same general methods used to synthesize S-(N-hydroxy N-methylcarbamoyl) glutathione and [$^{35}$S]S-(N-hydroxy N-methylcarbamoyl) glutathione described in Example 2 above.

The S-(N-Hydroxy N-methylcarbamoyl) glutathione[glycyl]-O-ethyl ester, for example, was prepared by incubating GSH[glycyl]O-ethyl ester (1.86 g hydrochloride salt, 5 mmol) and (N-hydroxy N-methylcarbamate) 4-chlorophenyl ester (0.20 g, 1 mmol) in 10 mL ethanol: H20 (1:1) at pH 7 (45° C.) under argon until there was no further detectable loss of (N-hydroxy N-methylcarbamate) 4-chlorophenyl ester (21 days), as monitored by silica gel TLC. The crude product was purified with the Whatman column described above in Example 1, using 0.25% acetic acid and 10% methanol in water as an eluting solvent (Retention Vol.=~ 660 mL).

Yield: 52%

H-1 300 MHz NMR ($D_2O$, pD 5.8, DSS); $-\delta 1.26$ (ethyl-CH$_3$, t, J=7.2 Hz), $\delta 2.13$ (Glu-C$\beta H_2$, m), $\delta 2.49$ (Glu-C$_\gamma H_2$, m), $\delta 3.13$ (Cys-C$\beta H_a$, q, J=8.0, 14.4 Hz), $\delta 3.26$ (N—CH$_3$, s), $\delta 3.37$ (Cys-C$\beta H_b$, q, J=4.9, 14.4 Hz), $\delta 3.76$ (Glu-C$\alpha$H, t, J=6.3 Hz), $\delta 4.00$ (Gly-CH$_2$, s), $\delta 4.21$ (ethyl-CH$_2$, q, J=7.2 Hz), $\delta 4.61$ (Cys-C$\alpha$H, q, J=4.9, 8.0 Hz)

Tandem FAB mass spectrum: m/z (rel. intensity) −409 [M+H]$^+$; 335 (49%) M-C(O)N(OH)CH$_3$+H]$^+$; 280 (19%) [M-C(O)CH$_2$CH$_2$CH (CO$_2$H)NH$_2$+2H]$^+$; 130 (100%) [Hz NCH(CO$_2$H)CH$_2$CH$_2$CO]$^+$; 104 (68%) [H$_3$NCH$_2$C(O)OCH$_2$CH$_3$]$^+$.

EXAMPLE 5

Synthesis of (N-Hydroxy N-Phenyl Carbamate)4-Chlorophenyl Ester (5a)

The (N-Hydroxy N-phenylcarbamate) 4-chlorophenyl ester was prepared by reacting N-phenylhydroxylamine with 4-chlorophenylchloroformate. N-Phenylhydroxylamine (2.02 g, 18 mmol) and K$_2$CO$_3$ (1.28 g, 9 mmol) were suspended in a mixture of diethyl ether (40 ml) and water (0.5 ml). While the suspension was stirred on ice, a solution of 4-chlorophenylchloroformate (3.5 g, 18 mmol) in dimethyl ether (20 ml) was added dropwise over 20 min. The reaction mixture was allowed to come to room temperature and the reaction was monitored until followed to completion (additional 90 min) by silica gel TLC (dimethyl ether:hexane (1:1)): $R_f$=0.42 (FeCl$_3$ staining). After the ether layer was decanted, the moist solids were washed with water (2×20 ml) and the solvent removed in vacuo.

The crude orange-yellow solid residue was dissolved in ethanol (~02 ml), brought to a cloud point by the addition of warm water (5 ml) and allowed to crystallize at room temperature. The fine white needle-like crystals of product were removed by suction filtration, washed thoroughly with 7.5% ethanol in water and recrystallized by the same procedure.

Yield: 91%

M.P: 116°–117° C.

UV (ethanol): −shoulder at λ=219 nm; $\lambda_{max}$=243 nm, $\epsilon_{243}$=17,500 m$^{-1}$cm$^{-1}$ IR (KBr, 1%): −3300, 1680, 1480, 1360, 1200, 860, 750 and 690 300 MHz $^1$H NMR (CDCl$_3$, TMS): $-\delta 7.10$ (d, J=8.7 Hz, 4-chlorophenyl ring m-H$_2$); $\delta 7.20$ (broad s, OH); $\delta 7.26$ (t, J=7.5 Hz, N-phenyl ring p-H); $\delta 7.34$ (d, J=8.7 Hz, 4-chlorophenyl ring o-H$_2$); $\delta 7.40$ (t, J=7.8 Hz, N-phenyl ring m-H$_2$); $\delta 7.54$ (d, J=8.1 Hz, N-phenyl ring o-H$_2$).

EXAMPLE 6

Synthesis of S-(N-Hydroxy N-Phenylcarbamoyl) Glutathione (6a)

S-(N-Hydroxy N-phenylcarbamoyl) glutathione was prepared by an acyl-interchange reaction between GSH and (N-hydroxy N-phenylcarbamate) 4-chlorophenyl ester. A stirring solution of GSH (307 mg, 1 mmol) in degassed and argon-saturated 1N NaOH (2 ml) under an argon atmosphere was brought nearly to a cloud point by the addition of ethanol (2 ml). This was followed by the dropwise addition of a solution of (N-hydroxy N-phenylcarbamate) 4-chlorophenyl ester (264 mg, 1 mmol) in ethanol (2 ml) over a period of ~5 min. The reaction vessel was sealed under argon and enclosed in foil. The mixture was stirred at room temperature until little GSH remained (88 hr), as judged by silica gel TLC (n-propanol: acetic acid:water (10:1:5):

$R_f$=0.57 (dark blue-purple spot by FeCl$_3$ staining, dark maroon by ninhydrin). The reaction mixture was brought to pH 3.5 by the addition of HCl, and the solvent removed in vacuo.

The crude residue was suspended in water (10 ml) and extracted with dimethyl ether (3×10 ml) to remove 4-chlorophenol and unreacted (N-hydroxy N-phenylcarbamate) 4-chlorophenyl ester. The combined ether phases were then back-extracted with water (10 ml). The combined aqueous phases were reduced to a minimum volume in vacuo and the residue purified by reverse-phase HPLC (Whatman Partisil C$_{18}$, 2.2×50 cm) using 0.25% acetic acid and 30% methanol in water as an eluting solvent (retention volume: ~50 ml).

The peak fractions were lyophilized to dryness to give the final product as a white powder.

Yield: ~50%

M.P.: 153° C. (dec.)

UV (water): $-\lambda_{max}$=253.5 nm, $\epsilon_{253.5}$=11,800 M$^{-1}$ cm$^{-1}$ 300 MHz $^1$H NMR (D$_2$O, pD 3.7, DSS): $-\delta$2.15 (m, Glu-C$\beta$H$_2$); $\delta$2.51 (m, Glu-C$_\gamma$H$_2$); $\delta$3.19 (q, J=8.3, 14.6 Hz, Cys-C$\beta$H$_a$); $\delta$3.44 (q, J=5.0, 14.6 Hz, Cys-C$\beta$H$_b$); $\delta$3.79 (t, J=6.3 Hz, Glu-C$\alpha$H); $\delta$3.96 (s, Gly-C$\alpha$H$_2$); $\delta$4.70 (q, J=5.0, 8.3 Hz, Cys-C$\alpha$H); $\delta$7.37 (m, aromatic $^1$H); $\delta$7.52 (m, aromatic 4H)

FAB mass spectrum: m/z 443 [M+H]$^+$.

EXAMPLE 7

Synthesis of N-Hydroxy-N-4-chlorophenyl carbamate 4-Chloro-phenyl Ester (5b)

This compound was prepared by the same general procedure used in Example 5 to prepare compound 5(a). The crude product was recrystallized from ethanol/water to give the final product as a tan solid.

Yield: ~65%

M.P.:=136°–138° C. Silica gel TLC (dimethyl ether:hexane (1:1)), $R_f$=0.42 (FeCl$_3$ stain) IR (KBr, 1%) –3240, 1710, 1580, 1470, 1330, 1290 cm$^{-1}$ 300 MHz $^1$H NMR (CDCl$_3$, TMS) $-\delta\epsilon$0.88 (broad s, OH); $\delta$7.12 (d, J=9.0 Hz, 4-chlorophenyl ring o-H$_2$); $\delta$7.36 (d, J=9.0 Hz, 4-chlorophenyl ring m-H$_2$); $\delta$7.37 (d, J=9.0 Hz, N-phenyl ring o-H$_2$); $\delta$7.52 (d, J=8.7 Hz, N-phenyl ring m-H$_2$)

HR EI-MS consistent with Cl$_2$C$_{13}$H$_9$NO$_3$. Anal. (Cl$_2$C$_{13}$H$_9$NO$_3$)C,H,N.

EXAMPLE 8

Synthesis of S-(N-Hydroxy-N-4-chlorophenylcarbamoyl) glutathione (6b)

To a stirring solution of compound 5(b) (37 mg, 0.12 mmoles) in ethanol (2 ml) was added a solution of GSH (191 mg, 0.62 mmoles) in argon-saturated water (2.0 ml), pH of 9.1. The reaction vessel was sealed under argon, enclosed in foil, and stirred at room temperature until little 5(b) remained (27 h), as judged by silica gel TLC (dimethyl ether:hexane (1:1)). The reaction mixture was worked up as described in Example 6 for compound 6a. The crude product was purified by reverse-phase HPLC (Waters µBondapak C$_{18}$, 0.78×30 cm) using 0.25% acetic acid and 35% methanol in water as an eluting solvent (retention volume: ~112 ml). The peak fractions were lyophilized to dryness to give the final product as a white powder. The product could alternatively be purified by passage through a G-15 column, using water as a running solvent.

Yield=34%

M.P.:=174° C. (dec.)

UV (water): $-\lambda_{max}$=259.5 nm, $\epsilon_{259.5}$13,489M$^{-1}$ cm$^{-1}$ 300 MHz $^1$H NMR (D$_2$O, pD 3.55, Reference to Gly-C$\alpha$H$_2$ peak) $-\delta$2.23 (m, Glu-C$\beta$H$_2$); $\delta$2.62 (m, Glu-C$_\gamma$H$_2$); $\delta$3.28 (q, J=8.1, 14.4 Hz, Cys-C$\beta$H$_a$); $\delta$3.54 (q, J=5.1, 14.4 Hz, Cys-C$\beta$H$_b$); $\delta$3.86 (t, J=6.3 Hz, Glu-C$\alpha$H); $\delta$3.98 (s, Gly-C$\alpha$H$_2$); $\delta$7.57 (q, J=9.0 Hz, aromatic ring 2H, meta to Cl); $\delta$7.62 (d, J=9.3 Hz, aromatic ring 2H, ortho to Cl)

HR FAB-MS consistent with ClC$_{17}$H$_{21}$N$_4$O$_8$S.

EXAMPLE 9

Synthesis of N-Hydroxy-N-4-bromophenyl carbamate 4-Chloro-phenylether (5c)

This compound was prepared by the same general procedure used in Example 5 to prepare compound 5(a). However, isolation of the desired product was complicated by the presence of significant amounts of side products. A solution of 4-chlorophenyl chloroformate (0.47 g, 2.46 mmol) in dimethyl ether (2 ml) was added dropwise to an ice-cold stirring mixture of N-4-bromophenyl hydroxylamine (0.46 g, 2.45 mmol), K$_2$CO$_3$ (0.17 g, 1.23 mmol), dimethyl ether (5 ml), and water (0.2 ml) over a period of 20 min. The reaction mixture was then stirred at room temperature for 20 min. Silica gel TLC (dimethyl ether:hexane (1:1)) of the reaction mixture indicated the absence of starting materials and the presence of at least two product species ($R_f$=0.4, 0.6). The reaction mixture was partitioned between dimethyl ether and water, the ether phase was dried over anhydrous NaS$_4$, and the solvent removed in vacuo to give an orange solid as a crude product (~0.8 g). The crude product was dissolved in a minimum of warm methanol, cooled to 4 C., and the undesired crystalline precipitate (~0.27 g) removed by filtration. The filtrate was concentrated in vacuo, brought to a cloud by the addition of water, and allowed to stand at room temperature for ~1 day. The resulting yellow needle like crystals were isolated by filtration and further purified by silica gel column chromatography (silica gel 60, EM Science ASTM 70–30 mesh; 2×10 cm), using CHCl$_3$ as an eluting solvent. The peak fractions were pooled and the solvent removed in vacuo to give a light yellow solid as the final product, having an $R_f$ of 0.34 by silica gel TLC (CHCl$_3$:ethyl acetate (9:1)).

Yield=20%

M.P.=160°–162° C.

IR (KBr, 1%) –3295, 1680, 1480, 1360, 1190, 860, 740 cm$^{-1}$

300 MHz $^1$H (CDCl$_3$, TMS). $\delta$6.79 (1H, s, OH), $\delta$7.11–7.38 (4H, m, 4-chlorophenyl), $\delta$7.45–7.54 (4H, m, 4-bromophenyl) HR EI-MS consistent with BrClC$_{13}$H$_9$NO$_3$ Anal. (BrClC$_{13}$H$_9$NO$_3$)C, H, N.

EXAMPLE 10

Synthesis of S-(N-Hydroxy-N-4-bromophenylcarbamoyl) glutathione (6c)

This compound was prepared by the same general procedure used in Example 6 to prepare compound 6a. The crude product was purified by reverse-phase HPLC (Whatman, Partisil C$_{18}$ 2.2×50 cm) using 0.25% acetic acid and 40% methanol in water as an eluting solvent (retention volume: ~665 ml).

Yield ~5%

300 MHz $^1$H NMR (D$_2$O, pH=3.7, DSS) —2.14 (m, Glu-C$\beta$H$_2$); $\delta$2.51 (m, Glu-C$_\gamma$H$_2$); $\delta$3.18 (q, J=8.4, 14.7 Hz, Cys-C$\alpha$H$_a$); $\delta$3.45 (q, J=4.8, 14.7 Hz, Cys-C$\beta$H$_b$); $\delta$3.76 (t, J=6.0 Hz, Glu-C$\alpha$H); $\delta$3.88 (s, Gly-C$\alpha$H$_2$); $\delta$7.64 (d, J=8.1 Hz, aromatic ring 2H, ortho to Br); $\delta$7.47 (d, J=8.1 Hz, aromatic ring 2H, meta to Br)

HR FAB-MS consistent with BrC$_{17}$H$_2$H$_{21}$N$_4$O$_8$S.

EXAMPLE 11

Synthesis of S-(N-Hydroxy-N-arylcarbamoyl) glutathione Diethyl Esters (6a(Et)$_2$, 6b(Et)$_2$ and 6c(Et)$_2$)

The diethyl esters of compounds 6a, 6b, and 6c were prepared by incubation of the latter compounds in ethanolic HCl overnight at room temperature.

EXAMPLE 12

Inhibition Studies with Glyoxalase I

In order to explore the structural basis of tight binding of S-(N-methyl-N-hydroxy carbamoyl) glutathione 2 to Glx I, the inhibition constants with yeast Glx I of S-(N-methylcarbamoyl)glutathione 2(a) and S-propionyl glutathione were determined and compared with those of the enediol analog 2 and S-D-lactoylglutathione 1. The chemical structures and the inhibition constants for various monoethyl ester compounds of the invention which were determined are shown in Scheme III below.

Clearly, the N—OH function of compound 2 makes an important contribution to binding (relative to an N—H group), because compound 2 binded 80-fold (about 2.6 Kcal/mole) more tightly to the active site of Glx I than its deoxy analog compound 2(a). In contrast, the lactoyl C—OH function of S-D-lactoyl glutathione contributed little to net binding (relative to a C—H group), because S-D-lactoylglutathione 1 and its deoxy analog 1(a) binded to the enzyme with similar affinities. Thus, preferential binding of the enediol analog by the enzyme can be partly attributed to preferential binding of the N—OH function. The conclusion that preferential binding is a property of the enzyme is based on the assumption that replacement of N—OH by N—H in 2 and replacement of C—OH by C—H in S-D-lactoylglutathione has a similar effect on the salvation energies of these ligands free in solution. Differential binding might reflect the presence of strong polar interactions between the active site and the C-2 hydroxyl group of bound compound 2. Indeed, a catalytic mechanism has been proposed for Glx I in which the active site zinc ion (Zn$^{+2}$) plays an electrophilic role in catalysis by indirectly interacting with the oxygen atoms of bound substrate. (Sellin, S., et al., J. Biol. Chem., 1982, 257:10023 (1982); Rosevear, P. R., et al., J. Biol. Chem. 258:6823 (1983)).

The glycyl-CO$_2^-$ of the enediol analog also appeared to contribute significantly to the preferential binding of compound 2 vs compound 1, based on the reported 10-fold higher affinity of the enzyme for compound 2 versus its glycyl-ethyl ester 2(Et), and the similar affinities of the enzyme for compound 1 and for its glycyl-ethyl ester 1(Et). (Hamilton et al., *Biochim. Biophys. Acta.* 1159:203 (1992)). Moreover, the glycyl-CO$_2^-$ of the substrate makes a similar contribution to transition-state stabilization during catalysis, as evidenced by the finding that $K_{cat}/K_m$ for GSH-methylglyoxal thiohemiacetal is 10-fold larger than that of its glycyl-ethyl ester. (Hamilton et al., *Biochim. Biophys. Acta.* 1159:203 (1992)). Taken together, these observations indicated that the high affinity of glyoxalase I for the enediol analog resulted from preferential binding of functional groups that are both near to, and far from, the reaction center.

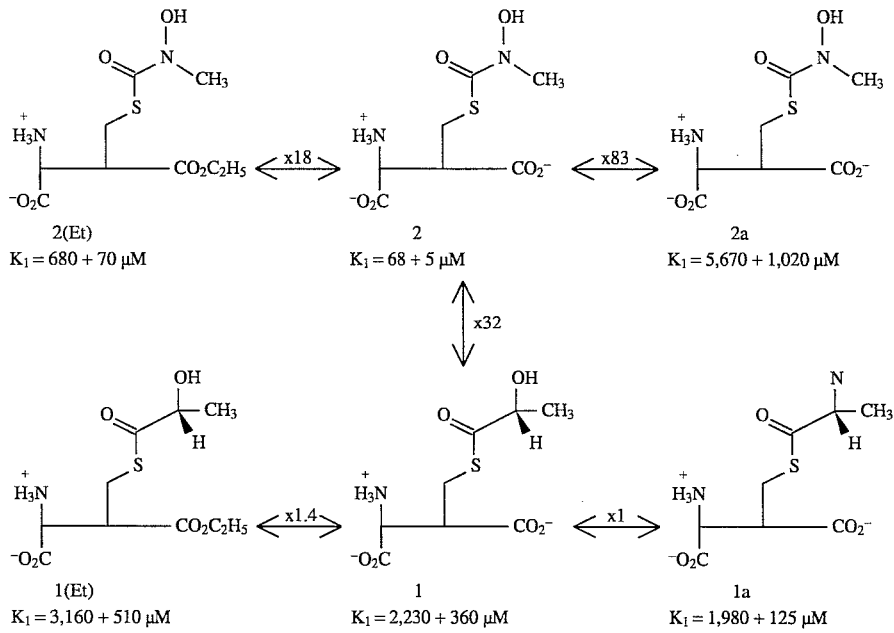

SCHEME III $^a$The peptide backbone of the glutathione moiety is symbolized by a horizontal line.

Inhibition constants were determined in phosphate buffer (50 mM, pH = 7), 25° C.

The same phenomenon appears to account for the high affinity of the transition-state analog nebularine hydrate for the active site of adenosine deaminase. (Kati et al., *Biochemistry* 31:7356 (1992)).

The three N-aryl derivatives (6(a-c)) shown in Scheme II were synthesized on the theory that they would bind more tightly than compound 2 to Glx I because of the presence of a hydrophobic binding pocket in the active site of Glx I. This was based on published structure-activity correlations indicating that hydrophobic interactions contribute to the binding of S-alkyl and S-aryl derivatives of GSH to yeast Glx I. (Vince, et al., *J. Med. Chem.* 14:402 (1971); Silipoet al., *Il Farmaco Ed. Sc.* 34:3 (1979)). In accordance with this prediction, the N-aryl derivatives proved to be linear competitive inhibitors of both yeast and human erythrocyte Glx I, with $K_i$ values much lower than those of compound 2 as is shown in Table 3.

TABLE 3

Enediol Analogs (GSC(O)N(OH)R) are Strong Competitive Inhibitors of Yeast and Human Erythrocyte Glyoxalase I[a]

| Compound | R | $\pi$[b] | $K_i$ ($\mu$M) Yeast | Erythrocytes |
|---|---|---|---|---|
| 2 | $CH_3$ | 0.5 | 68 ± 5[c] | 1.95 ± 0.21 |
| 6(a) | $C_6H_5$ | 2.13 | 11 ± 1 | 0.18 ± 0.010 |
| 6(b) | $C_6H_4Cl$ | 3.04 | 3.6 ± 0.3 | 0.053 ± 0.005 |
| 6(c) | $C_6H_4Br$ | 3.25 | 1.2 ± 0.2 | 0.016 ± 0.001 |

[a]Phosphate buffer (50 mM, pH 7), 25° C.
[b]Hansch hydrophobicity constants obtained from Kati et al., Biochemistry 31:7356 (1992)
[c]From Hamilton et al., J. Biol. Chem. 267:24933 (1992).

Clearly, hydrophobic interactions contribute to the binding, on the basis that the magnitudes of the $K_i$ values decrease with increasing hydrophobicity of the N-substituents as follows:

$$\text{Yeast glyoxalase I log } K_i = -0.58 \pi - 3.82 \quad (2)$$

$$\text{Human glyoxalase I log } K_i = -0.69 \pi 0.69 \quad (3)$$

The similar magnitudes of the slope terms for the two equations indicated that the active sites of the yeast and human enzymes have similar hydrophobicities (~58% and 69% that of n-octanol). It is not clear why the $K_i$ values for the human enzyme are 35- to 75-fold lower than those for the yeast enzyme (Table 3). This difference appears to be due to stronger polar interactions between the bound enediol analogs and the active site of the human enzyme, judging from the different intercept terms of equations 2 and 3. Among the compounds prepared, the most hydrophobic enediol analog 6(c) is the strongest competitive inhibitor of glyoxalase I yet reported.

EXAMPLE 13

Substrate Studies with Glyoxalase II

The enediol analogues of the invention also proved to be slow substrates for a crude commercial preparation of bovine liver Glx II. The results are shown in Table 4.

TABLE 4

Enediol Analogs (GSC(O)N(OH)R) are Slow Substrates for Bovine Liver Glyoxalase II[a]

| Comp. | R | $V_m$[b] (rel.) | $K_m$ ($\mu$M) | $K_i$[c] ($\mu$M) |
|---|---|---|---|---|
| 2 | $CH_3$ | (1.7 ± 0.1) × $10^{-5}$ | 478 ± 75 | 426 ± 77 |
| 6(a) | $C_6H_5$ | (0.46 ± 0.01) × $10^{-5}$ | 13 ± 2 | 11 ± 1.2 |
| 6(b) | $C_6H_4Cl$ | (1.5 ± 0.3) × $10^{-5}$ | d | 3.4 ± 0.8 |
| 6(c) | $C_6H_4Br$ | (2.1 ± 0.4) × $10^{-5}$ | d | 1.2 ± 0.4 |

[a]HEPES buffer (100 mM, pH 7.4), 25° C.
[b]Listed values are relative to $V_m$ for S-D-lactoylglutathione.
[c]Inhibition constants obtained from using the enediol analogs as competitive inhibitors of the hydrolysis of S-D-lactoylglutathione by glyoxalase II.
[d]Could not be measured because accurate initial rates could not be obtained at substrate concentrations less than 3 $\mu$M.

In order to confirm that the catalyzed hydrolysis of these compounds was due to Glx II, each compound was tested as a competitive inhibitor of the hydrolysis of S-D-lactoylglutathione by the enzyme preparation. The similarity of the observed inhibition constants of compound 2 and compound 6a to their respective $K_m$, values as substrates indicated that a single enzyme species is responsible for the hydrolysis of S-D-lactoylglutathione and the carbamoyl esters. As in the case of Glx I, hydrophobic interactions contribute significantly to active site binding as shown in equation (4):

$$\log K_i = -0.88 \pi - 2.96, r = 0.993 \quad (4)$$

The $V_{max}$ values of the enediol analogues were small in comparison to that of S-D-lactoylglutathione, perhaps reflecting the greater intrinsic stability of the resonance stabilized carbamoyl ester function.

S-(N-Aryl N-hydroxycarbamoyl)glutathione derivatives were thus found to be a new class of tight-binding inhibitors of Glx I that also serve as substrates for the hydrolase Glx II. Their ability to bind tightly to the active site of Glx I results from a combination of their stereoelectronic similarity to the tightly bound enediol(ate) intermediate that forms along the reaction pathway of the enzyme and their ability to interact with a hydrophobic binding pocket in the active site.

EXAMPLE 14

Erythrocyte Uptake of S-(N-Hydroxy N-methylcarbamoyl) glutathione (2) and Its O-Ethyl Ester (2(Et))

In order to test the ability of human erythrocytes to take up the above enediol and its ethyl ester derivative, suspensions of washed human erythrocytes were separately incubated with [$^{35}$S] GSH, [$^{35}$S]S-(N-hydroxy N-methylcarbamoyl) glutathione, and with [$^{35}$S] S-(N-hydroxy N-methylcarbamoyl) glutathione[glycyl]-O-ethyl ester. The tests were conducted with 50:50 (v:v) erythrocytes in PBS buffer at 37° C. in the presence of 8.5 mM extracellular [$^{35}$S] labeled compounds.

In all three cases, the total intracellular concentration of the $^{35}$S-labeled species underwent a slow nonlinear increase over a period of 48 h. Consistent with passive diffusion of these molecules across the cell membrane, the rates of transfer of total $^{35}$S-labeled species into erythrocytes over a 12 h incubation period were found to be a linear function of the extracellular concentration in the range of 1–10 mM; i.e., there was no evidence for saturation kinetics. The finding that the diffusion rate of [$^{35}$S] 2(Et) is ~2-fold greater than that of [$^{35}$S] 2 supports the hypothesis that ethylation of the glycyl-CO$_2$ of 2 facilitates transfer across the cell membrane.

Chromatographic analysis of the $^{35}$S-labeled species in the extracellular and intracellular fractions over the course of the 48 h incubation was consistent with intracellular hydrolysis of [$^{35}$S]2 (to give [$^{35}$S] GSH) and [$^{35}$S] 1(Et) (to give [$^{35}$S] 1). (See, Table 5): (1) For the control experiment using [$^{35}$S] GSH the intracellular [$^{35}$S] GSH underwent significant oxidation to [$^{35}$S] GSSG over the course of the 48 h incubation. Therefore, the total intracellular [$^{35}$S]GSH+[$^{35}$S]GSSG could rise from the transport of either one or both of these species, probably followed by disulfide interchange with endogenous unlabeled glutathione/GSSG. (2) For the experiment using [$^{35}$S] 2, there was a progressive increase in the intracellular concentration of this species as a function of time, indicating that [$^{35}$S] 2 is transported intact across the cell membrane. A small increase in the intracellular [$^{35}$S]glutathione+[$^{35}$S]GSSG to a final concentration of 0.04 mM, probably reflects the Glx II-catalyzed hydrolysis of intracellular [$^{35}$S] 2. (3) For the experiment using [$^{35}$S] 2(Et), the extracellular fractions showed a time-dependent increase in the concentration of [$^{35}$S] 2, from 1.3 mM to 1.9 mM, due to the spontaneous hydrolysis of extracellular [$^{35}$S] 2(Et) over the course of the 48 h incubation. The intracellular fractions showed a progressive increase in both [$^{35}$S] 2(Et) and [$^{35}$S] 2, to final concentrations of 0.39 mM and 0.24 mM, respectively. Thus, some of the intracellular [$^{35}$S] 2 probably arises from the catalyzed hydrolysis of intracellular [$^{35}$S] 2(Et) since the final concentration of intracellular [$^{35}$S] 2 (0.24 mM) was about 3-fold greater than that expected from the import of contaminating [$^{35}$S] 2 from the extracellular space.

These observations show that glutathione-based inhibitors of Glx I, such as the compounds of this invention, can be delivered into cells as their alkyl esters. These data are shown in Table 5 below.

TABLE 5

Time-Dependent Change in the Distribution of $^{35}$S Labeled Species in Erythrocytes

| System | Incubation Time (hours) | | | | | |
|---|---|---|---|---|---|---|
| | 0 | 6 | 12 | 24 | 36 | 48 |
| [$^{35}$S] GSH: | | | | | | |
| Intracellular species (mM) | | | | | | |
| Total | ~0 | 0.04 | 0.05 | 0.13 | 0.28 | 0.48 |
| [$^{35}$S] GSH | n.d. | 0.02 | n.d. | n.d. | n.d. | 0.10 |
| [$^{35}$S] GSSG | n.d. | 0.02 | n.d. | n.d. | n.d. | 0.27 |
| Extracellular species (mM) | | | | | | |
| Total | 8.48 | 8.56 | 8.61 | 8.38 | 8.37 | 8.23 |
| [$^{35}$S] GSH | 7.95 | 7.90 | n.d. | n.d. | n.d. | 5.31 |
| [$^{35}$S] GSSG | 0.43 | 0.53 | n.d. | n.d. | n.d. | 2.49 |
| [$^{35}$S] ●  | | | | | | |
| Intracellular species (mM) | | | | | | |
| Total | ~0 | 0.02 | 0.03 | 0.12 | 0.31 | 0.44 |
| [$^{35}$S] ● | n.d. | n.d. | ~0.01 | 0.08 | 0.26 | 0.37 |
| [$^{35}$S] GSH + [$^{35}$S] GSSG | n.d. | n.d. | ~0.01 | 0.03 | 0.04 | 0.04 |
| Extracellular species (mM) | | | | | | |
| Total | 8.44 | 8.57 | 8.67 | 8.24 | 8.24 | 8.50 |
| [$^{35}$S] ● | 8.20 | 8.32 | 8.39 | 7.96 | 7.96 | 8.19 |
| [$^{35}$S] GSH + [$^{35}$S] GSSG | ~0.01 | 0.15 | 0.14 | 0.14 | 0.13 | 0.14 |
| [$^{35}$S] ■: | | | | | | |
| Intracellular species (mM) | | | | | | |
| Total | ~0.01 | 0.05 | 0.07 | 0.20 | 0.45 | 0.67 |
| [$^{35}$S] ■ | n.d. | ~0.01 | 0.03 | 0.12 | 0.28 | 0.39 |
| [$^{35}$S] ● | n.d. | ~0.01 | 0.02 | 0.05 | 0.14 | 0.24 |
| Extracellular species (mM) | | | | | | |
| Total | 8.54 | 8.60 | 8.62 | 8.49 | 8.09 | 7.90 |
| [$^{35}$S] ■ | 7.22 | 7.17 | 7.02 | 6.62 | 6.01 | 5.70 |
| [$^{35}$S] ● | 1.27 | 1.27 | 1.42 | 1.65 | 1.83 | 1.89 |

● S-(N-hydroxy N-methylcarbamoyl) glutathione
■ S-(N-hydroxy N-methylcarbamoyl) glutathioneglycyl-O-ethyl ester

EXAMPLE 16

Compounds 2 and (6c) Inhibit the Growth of Different Tumor Cell Lines in Culture The strongest inhibitor (S-(N-hydroxy N-4 bromophenyl carbamoyl) glutathione (6c), Ki=0.016 μM), and the weakest inhibitor (S-(N-hydroxy N-methylcarbamoyl) glutathione (2), Ki=1.95 μM) of human Glx I were submitted to the National Cancer Institute Developmental Therapeutics program for testing against their standard panel of human tumor cells in culture. The results obtained are summarized in Table 6.

TABLE 6

Cell Growth Inhibition Properties of Compounds 2 and 6c against Selected Tumor Cell Lines (48 hrs. incubation)

| | Compound 2 | | | Compound 6c | | |
|---|---|---|---|---|---|---|
| Cell Line | GI$^a$ (μM) | TGI$^b$ (μM) | LC$_{50}$$^c$ (μM) | GI$^a$ (μM) | TGI$^b$ (μM) | LC$_{50}$$^c$ (μM) |
| Renal Cancer (ACHN) | >1000 | >1000 | >1000 | 25 | ~200 | >1000 |
| Non-Small Cell Lung Cancer (HOP-18) | 630 | >1000 | >1000 | 40 | ~250 | >1000 |
| Colon Cancer (KMZOLZ) | >1000 | >1000 | >1000 | 40 | ~320 | >1000 |
| Ovarian Cancer (SK-OV-3) | 316 | ~1000 | >1000 | 32 | ~250 | >1000 |
| CNS Cancer (SNB-75) | 630 | >1000 | >1000 | 63 | ~1000 | >1000 |
| Melanoma (UACC-62) | >1000 | >1000 | >1000 | 126 | >1000 | >1000 |

$^a$Concentration for 50% cell growth inhibition versus no-drug controls.
$^b$Concentration for total cell growth inhibition versus no-drug controls.
$^c$Concentration for 50% cell kill.

The compounds 2 and 6(b) of this invention were found to inhibit the growth of various human tumor cell lines in culture, as shown in Table 6 above. Importantly, the strongest inhibitor of Glx I amongst the present compounds (6c), proved to have lower $GI_{50}$ and TGI values than the weakest of the compounds (2). This is consistent with the postulate that the inhibition of cell growth is due to blockage of Glx I enzyme activity.

When human renal cancer cells (ACHN cells) were exposed to compound 2, no significant effect was seen at concentrations lower than $10^{-3}M$. At this concentration, compound 2 inhibited cell growth by about 40%. Compound 6(c) was more active in that its inhibitory effect started to be seen at a concentration of $10^{-5}M$. At this concentration, compound 6(c) produced a 30% inhibition of cell growth, and at $10^{-4}M$, it yielded about 95% cell growth inhibition.

With non-small cell human lung cancer cells (HOP-18 cells), a similar pattern was observed for the two compounds, except that compound 2 appeared to be more active at a concentration of $10^{-3}M$, producing upward of 65% cell growth inhibition. Compound 6(c) yielded about 15% cell growth inhibition at concentrations of $10^{-6}$ to $10^{-5}M$, whereas it produced an inhibition of about 80% at $10^{-4}M$.

When the two compounds were tested with human colon cancer cells (KMZOL2 cells), again compound 6(c) was more active in inhibiting cell growth than compound 2. Compound 2 had no significant effect at concentrations of $10^{-4}$ and below. At this concentration it produced slightly less than a 30% inhibition of cell growth. Compound 6 showed about 10% inhibition at concentrations of $10^{-6}$ and $10^{-5}$, and an 80% inhibition of cell growth at $10^{-4}M$.

The effect on human ovarian cancer cells (SK-OV-3 cells) was more striking. Both compounds reached high inhibitory activities, compound 2 inhibited cell growth by 20% at $10^{-4}M$ and by greater than 90% at $10^{-3}M$. Compound 6(c) was active at much lower concentrations. At $10^{-6}M$, the inhibition was almost 40%, at $10^{-5}$ the inhibition was about 30%, and at $10^{-4}M$ the inhibition of cell growth was over 80% when compared with the original value before addition of the compound.

In the case of CNS human cancer cells, compound 2 showed low inhibitory activity (less than 10%) at concentrations of $10^{-4}M$ or lower but an interesting 60% inhibition of cell growth at $10^{-3}M$. Compound 6(c) showed about 20% inhibition at $10^{-6}M$ and $10^{-5}M$, and 60% inhibition of cell growth at $10^{-4}M$.

When placed in the presence of human melanoma cells (UACC-62 cells), compound 2 was ineffective at concentrations of $10^{-4}$ or lower and inhibited cell growth by 30% at $10^{-3}M$. Compound 6(c) produced minimal inhibition at $10^{-6}M$ and lower concentrations, and about 20% inhibition of cell growth at $10^{-5}M$, and 50% at $10^{-4}M$.

Clearly, although both compounds show cell growth inhibitory activities, compound 6(c) is the better inhibitor and anticancer agent, at lower concentrations, particularly when applied to the treatment of human renal cancer, non-small cell lung cancer, colon cancer, and ovarian cancer. However, there was no evidence of significant cytotoxicity (cell killing) by either compound. That is, after 48 hrs. in the presence of the inhibitor, the cell density was equal to, or greater than, that at the beginning of the test (t=0). The glycyl monoethyl esters of compounds 2 and 6c were found to be only somewhat more cytostatic than the unethylated species (data not shown).

EXAMPLE 17

The Diethyl Esters of Compounds 6a, 6b and 6c are More Toxic to Human Leukemia 60 (HL60) Cells than the Corresponding Unethylated Derivatives The observation that compounds 2 and 6(c) inhibit tumor cell growth, but were not strongly cytotoxic to tumor cells at the concentrations tested, prompted the synthesis of diethyl esters of compounds 6(a), 6(b), and 6(c). These derivatives were then tested with human leukemia cells (HL60 cells) grown in RPMI/fetal calf serum medium at 37° C. In all cases, the diethyl esters $6(a)(Et)_2$, $6(b)(Et)_2$, and $6(c)(Et)_2$ were found to be more toxic to human leukemia cells than their corresponding unethylated species as shown in Table 7 below.

TABLE 7

Cell Growth Inhibition Properties of Compounds (6a), (6b), and (6c) and their Diethyl Esters against Human Leukemia 60 Cells (72 hr. incubation)

| Compound | $GI^a$ (μM) | $TGI^b$ (μM) | $LC_{50}^c$ (μM) | $Ki^d$ (μM) |
|---|---|---|---|---|
| 6a $(E_t)_2$ | 63 | 126 | 200 | >1000 |
| 6b $(E_t)_2$ | 16 | 32 | 50 | >1000 |
| 6c $(E_t)_2$ | 5 | 18 | 32 | >1000 |
| 6a | ~100 | >1000 | >1000 | 0.18 |
| 6b | ~100 | >1000 | >1000 | 0.053 |
| 6c | 20 | 63 | ~300 | 0.016 |

$^a$Concentration for 50% cell growth inhibition versus no-drug controls.
$^b$Concentration for total cell growth inhibition versus no-drug controls.
$^c$Concentration for 50% cell kill.
$^d$Competitive inhibition constants with human erythrocyte glyoxalase I.

In addition, the diethyl esters found to have the lowest LC50 values corresponded to the enediol analogues having the lowest inhibition constants (Ki) for human Glx I.

Taken together, these results suggest that cytotoxicity results from the following:

a) Rapid transport of the diethyl ester derivatives into leukemia cells.

b) Catalyzed hydrolysis of the diethyl ester derivatives to free the unesterified inhibitor.

c) Inhibition of glyoxalase I.

d) Increased concentrations of intracellular methylglyoxal.

Compound $(6a(Et)_2)$ was found to produce about 100% cell killing of human leukemia 60 (HL60) cells at a concentration of 250 to 300 μM, whereas the same concentration produced only inhibition of cell growth to about 50–80% in normal human VA-2 fibroblasts. This effect might be explained by abnormally low levels of Glx II in HL60 cells as well as a reduced ability of these cells to hydrolyze the inhibitor. In support of this hypothesis, S-p-Bromobenzyl glutathione, was found to be equally toxic to both HL60 cells and fibroblasts (LC50=50 μM). The latter compound is a tight binding inhibitor of human Glx I (Ki=0.27 μM), but unlike compound 6a, it cannot be hydrolyzed by Glx II.

Taken together, the experimental results reported herein support the effectiveness of the present class of compounds as tumor-selective anti-cancer agents, particularly as being suitable anti-leukemic, anti-ovarian cancer, anti-renal cancer, anti-non-small cell lung cancer, anti-colon cancer, anti-CNS cancer, and anti-melanoma agents. These compounds are expected to also be effective as anti-cancer agents for other types of cancers, such as cancer of the bladder, prostate, testis, breast, and brain, among others.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A compound of the formula

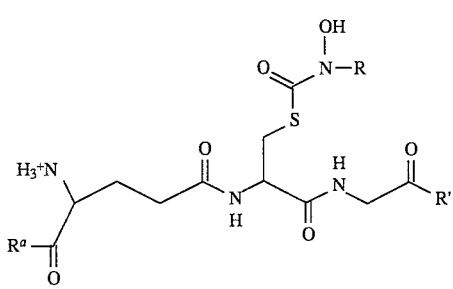

wherein

R is hydrogen, $(C_1-C_{18})$alkyl, $(C_6-C_{20})$aryl, or $(C_6-C_{20})$aryl substituted with halogen or $(C_1-C_{18})$alkyl;

R' is hydroxyl, or —$O(C_1-C_{18})$alkyl; and $R^a$ is an —$O(C_1-C_{18})$alkyl, pharmaceutically acceptable salts thereof, or mixtures thereof.

2. A compound of the formula

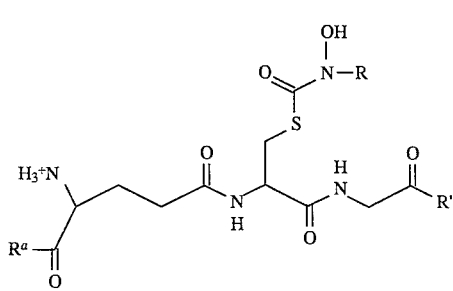

wherein

R is hydrogen, $(C_1-C_{18})$alkyl, $(C_6-C_{20})$aryl, or $(C_6-C_{20})$aryl substituted with halogen or $(C_1-C_{18})$alkyl;

R' is hydroxyl or —$O(C_1-C_{18})$alkyl; and $R^a$ is hydroxyl, pharmaceutically acceptable salts thereof, or mixtures thereof.

3. The compound of claim 1 wherein R is hydrogen, methyl, phenyl or bromo-substituted phenyl.

4. The compound of claim 1 wherein R' is an —O(C1–C18)alkyl.

5. The compound of claim 3 wherein R' is an —O(C1–C6)alkyl.

6. The compound of claim 4 wherein R' is an —O-ethyl.

7. A pharmaceutical composition of matter comprising the compound of claim 2 in an amount effective for preventing or inhibiting the growth and proliferation of neoplastic cells or tumors; and a pharmaceutically acceptable carrier therefor.

8. The composition of claim 6, wherein the compound is present in an amount of between about 0.01 and 99.00 wt % of the composition.

9. The composition of claim 6, in tablet, solution, capsule or suppository form.

10. The composition of claim 6, in unit dosage form.

11. The composition of claim 6, in injectable form.

12. A method of inhibiting the growth and proliferation of, or eliminating existing neoplastic cells having low glyoxalase II activity comprising treating the cells with the compound of claim 1 or 2 in an amount effective for inhibiting the growth and proliferation of, or eliminating existing neoplastic cells.

13. A method of inhibiting the growth and proliferation of, or eliminating existing neoplastic cells in a subject comprising administering to the subject in need of such treatment the composition of claim 7 in an amount effective for inhibiting the growth and proliferation of, or eliminating existing neoplastic cells.

14. The method of claim 13, wherein the composition is administered in an amount of about 0.001 to 100 mg/kg body weight/dose.

15. The method of claim 13, wherein the composition is administered orally, intravenously, subcutaneously, transdermally, intramuscularly or intraperitoneally.

16. The method of claim 15, wherein the composition is administered intravenously.

17. The method of claim 13, wherein the neoplastic cells comprise renal, ovarian, colon, non-small cell lung cancer, CNS or leukemia cells.

18. The method of claim 13 wherein the subject is a human.

19. A method of inhibiting the growth of an existing malignant tumor in a subject comprising administering to the subject in need of such treatment the composition of claim 7 in an amount effective for inhibiting the growth of an existing malignant tumor.

20. The method of claim 19, wherein the composition is administered in an amount of about 0.001 to 100 mg/kg body weight/dose.

21. The method of claim 19, wherein the composition is administered orally, intravenously, subcutaneously, transdermally, intramuscularly or intraperitoneally.

22. The method of claim 21, wherein the composition is administered intravenously.

23. The method of claim 19 wherein the malignant tumor comprises renal, ovarian, colon, non-small cell lung cancer, CNS or leukemia cells.

24. A method of inhibiting the growth and proliferation of, or eliminating existing neoplastic cells in a mammalian tissue comprising a neoplastic cell, wherein the method comprises treating the tissue in vitro with the compound of claim 1 or 2 in an amount effective for inhibiting the growth and proliferation of, or eliminating the existing neoplastic cells.

25. A method of inhibiting the growth and proliferation of, or eliminating an existing tumor in a mammalian tissue comprising a tumor, wherein the method comprises treating the tissue in vitro with the compound of claim 1 or 2 in an amount effective for inhibiting the growth and proliferation of, or eliminating the existing tumor.

* * * * *